(12) United States Patent
Hidaka et al.

(10) Patent No.: US 10,646,125 B2
(45) Date of Patent: May 12, 2020

(54) BIOLOGICAL INFORMATION MEASUREMENT APPARATUS

(71) Applicant: KYOCERA Corporation, Kyoto (JP)

(72) Inventors: Mizuho Hidaka, Kawasaki (JP); Norikazu Morioka, Tama (JP); Asao Hirano, Koganei (JP)

(73) Assignee: KYOCERA Corporation, Kyoto (JP)

( * ) Notice: Subject to any disclaimer, the term of this patent is extended or adjusted under 35 U.S.C. 154(b) by 181 days.

(21) Appl. No.: 15/505,756

(22) PCT Filed: Sep. 8, 2015

(86) PCT No.: PCT/JP2015/004570
§ 371 (c)(1),
(2) Date: Feb. 22, 2017

(87) PCT Pub. No.: WO2016/038887
PCT Pub. Date: Mar. 17, 2016

(65) Prior Publication Data
US 2018/0214041 A1    Aug. 2, 2018

(30) Foreign Application Priority Data
Sep. 8, 2014   (JP) ................................. 2014-182378

(51) Int. Cl.
| | |
|---|---|
| *A61B 5/00* | (2006.01) |
| *A61B 5/024* | (2006.01) |
| *A61B 5/02* | (2006.01) |
| *H04R 25/00* | (2006.01) |
| *H04R 1/10* | (2006.01) |

(52) U.S. Cl.
CPC ............ *A61B 5/02427* (2013.01); *A61B 5/02* (2013.01); *A61B 5/024* (2013.01); *A61B 5/02438* (2013.01); *A61B 5/6817* (2013.01); *H04R 25/30* (2013.01); *H04R 1/1016* (2013.01)

(58) Field of Classification Search
CPC ... A61B 5/6817; A61B 5/1455; A61B 5/6815; H04R 1/1016
See application file for complete search history.

(56) References Cited

U.S. PATENT DOCUMENTS

| | | | |
|---|---|---|---|
| 2008/0220535 A1 | 9/2008 | Leboeuf et al. | |
| 2009/0299215 A1* | 12/2009 | Zhang ................... | H04R 25/30 600/559 |

(Continued)

FOREIGN PATENT DOCUMENTS

| | | |
|---|---|---|
| EP | 2 536 167 A1 | 12/2012 |
| JP | S58-198329 A | 11/1983 |

(Continued)

OTHER PUBLICATIONS

International Search Report issued in PCT/JP2015/004570; dated Nov. 24, 2015.

(Continued)

*Primary Examiner* — Sean P Dougherty
*Assistant Examiner* — David Joseph Fernandez-Fidalgo
(74) *Attorney, Agent, or Firm* — Studebaker & Brackett PC

(57) ABSTRACT

A biological information measurement apparatus includes a biological sensor and an insertion portion, and the biological sensor is disposed at a position opposite the concha when the insertion portion is inserted in the external ear canal.

5 Claims, 6 Drawing Sheets

(56) References Cited

U.S. PATENT DOCUMENTS

| | | | |
|---|---|---|---|
| 2012/0283578 A1 | 11/2012 | Leboeuf et al. | |
| 2013/0131519 A1* | 5/2013 | LeBoeuf | A61B 5/0077 600/476 |
| 2013/0336495 A1 | 12/2013 | Burgett et al. | |

FOREIGN PATENT DOCUMENTS

| | | |
|---|---|---|
| JP | 2000-092582 A | 3/2000 |
| JP | 2008-168051 A | 7/2008 |
| JP | 2013-118904 A | 6/2013 |
| WO | 2012/103273 A2 | 8/2012 |
| WO | 2014/092932 A1 | 6/2014 |

OTHER PUBLICATIONS

Written Opinion issued in PCT/JP2015/004570; dated Nov. 24, 2015; with English language Concise Explanation.

The extended European search report issued by the European Patent Office dated Jan. 8, 2018, which corresponds to EP15840904.5-1115 and is related to U.S. Appl. No. 15/505,756.

Chen-Hung Huang et al., "Earbud-type earphone modeling and measurement by head and torso simulator", Applied Acoustics, May 1, 2012, pp. 461-469, vol. 73, No. 5, Elsevier.

* cited by examiner

FIG. 5

|  | Biological information measurement apparatus of this disclosure | Known method 1 (finger) | Known method 2 (back side of the antitragus) |
|---|---|---|---|
| Pulse acquisition rate | 100% | 96% | 92% |
| Average pulse (n = 50) | 70.8 | 70.6 | 73.0 |

BIOLOGICAL INFORMATION MEASUREMENT APPARATUS

CROSS-REFERENCE TO RELATED APPLICATION

This application claims priority to and the benefit of Japanese Patent Application No. 2014-182378 filed Sep. 8, 2014, the entire contents of which are incorporated herein by reference.

TECHNICAL FIELD

This disclosure relates to a biological information measurement apparatus.

BACKGROUND

Biological information measurement apparatuses that measure biological information of a user, such as pulse, have been proposed. Biological information is measured by a variety of methods using a biological information measurement apparatus.

SUMMARY

A biological information measurement apparatus according to this disclosure includes: a biological sensor and an insertion portion; such that the biological sensor is disposed at a position opposite a concha when the insertion portion is inserted in an external ear canal.

BRIEF DESCRIPTION OF THE DRAWINGS

In the accompanying drawings:

FIG. 5 compares the pulse measurement results for the biological information measurement apparatus according to Embodiment 1 and a known apparatus.

DETAILED DESCRIPTION

In a known pulse measurement apparatus, however, the position of the earphone might shift due to body movement or the like. If the position of the biological information measurement apparatus changes, noise is included in the biological information measured using the sensor, making it difficult to measure biological information accurately.

Therefore, it would be helpful to provide a biological information measurement apparatus that can improve the measurement accuracy of biological information.

The following describes embodiments of the disclosed apparatus.

In general terms, a biological information measurement apparatus 100 according to Embodiment 1 is provided with an earpiece 110 that includes a biological sensor 111 and an insertion portion 112. The earpiece 110 is worn in a user's ear.

Figure 1:
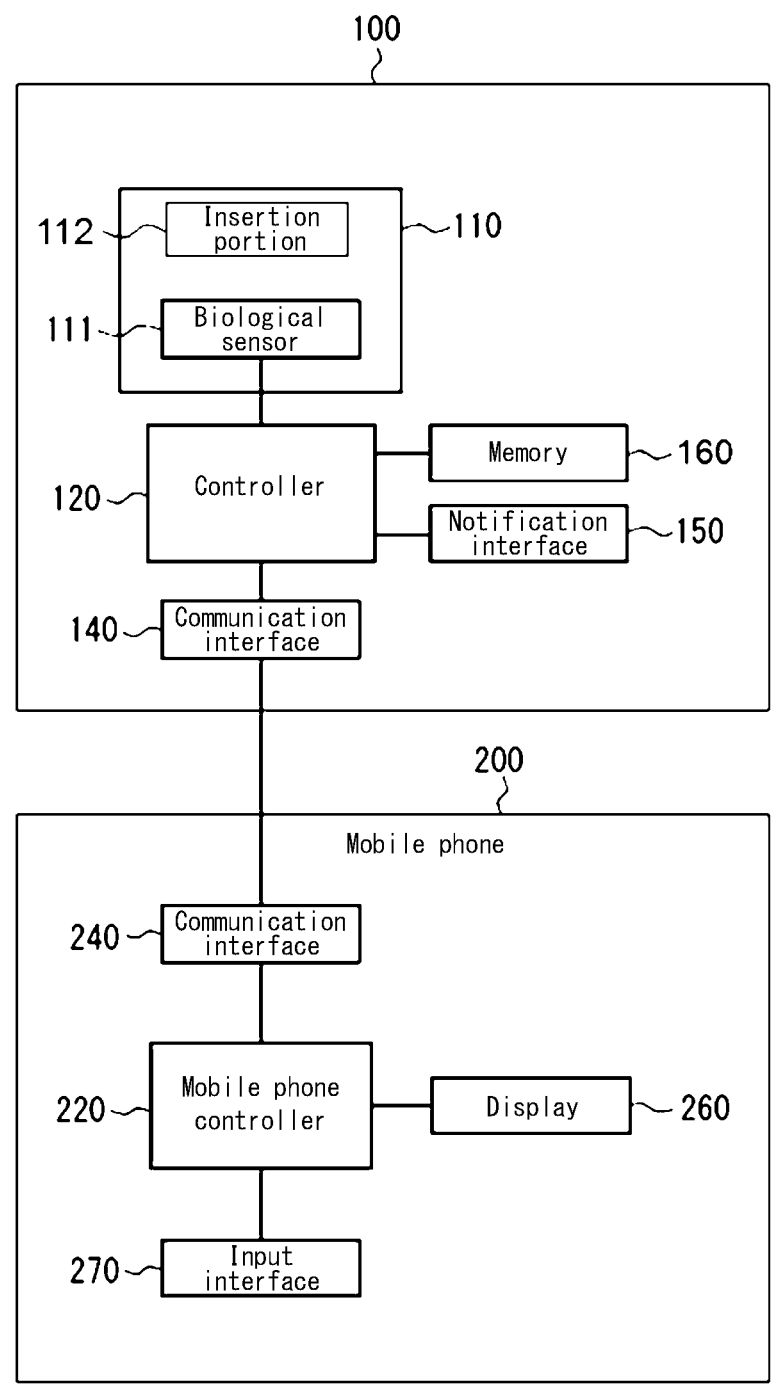
FIG. 1 is a functional block diagram of a section of the biological information measurement apparatus according to Embodiment 1.

FIG. 1 is a functional block diagram of a section of the biological information measurement apparatus 100 according to Embodiment 1. The biological information measurement apparatus 100 according to this embodiment is provided with the earpiece 110, a controller 120, a memory 160, a communication interface 140, and a notification interface 150. The biological information measurement apparatus 100 measures biological information using the biological sensor 111 provided in the earpiece 110 after the user has inserted the insertion portion 112 into the external ear canal.

The biological information may be any biological information that can be measured using the biological sensor 111 provided in the earpiece 110. In this embodiment, as one example, the biological information measurement apparatus 100 is described below as measuring the user's pulse.

Figure 2A:
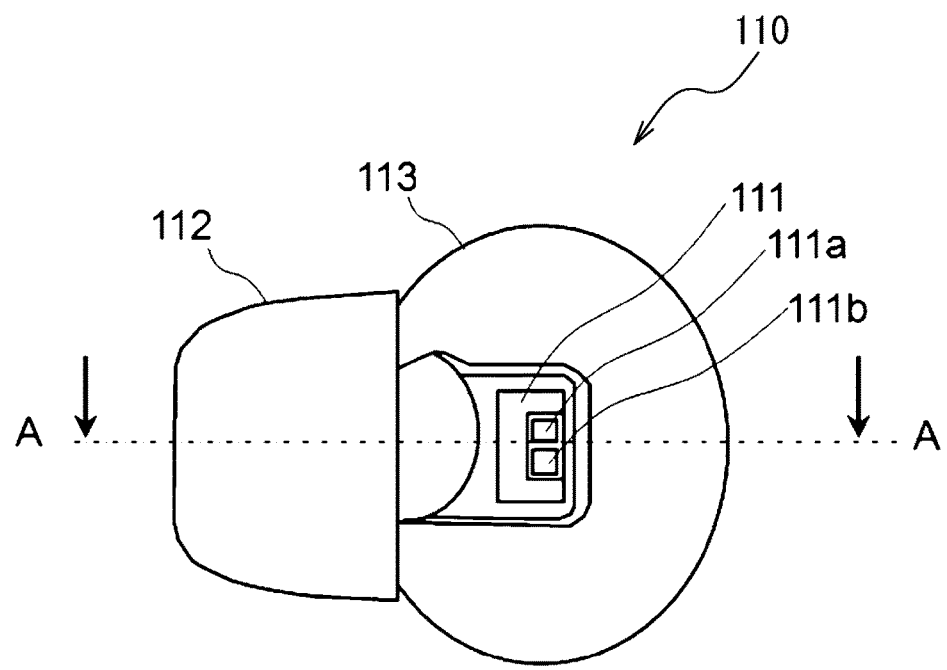
FIG. 2A schematically illustrates the structure of the biological information measurement apparatus according to Embodiment 1.
Figure 2B:
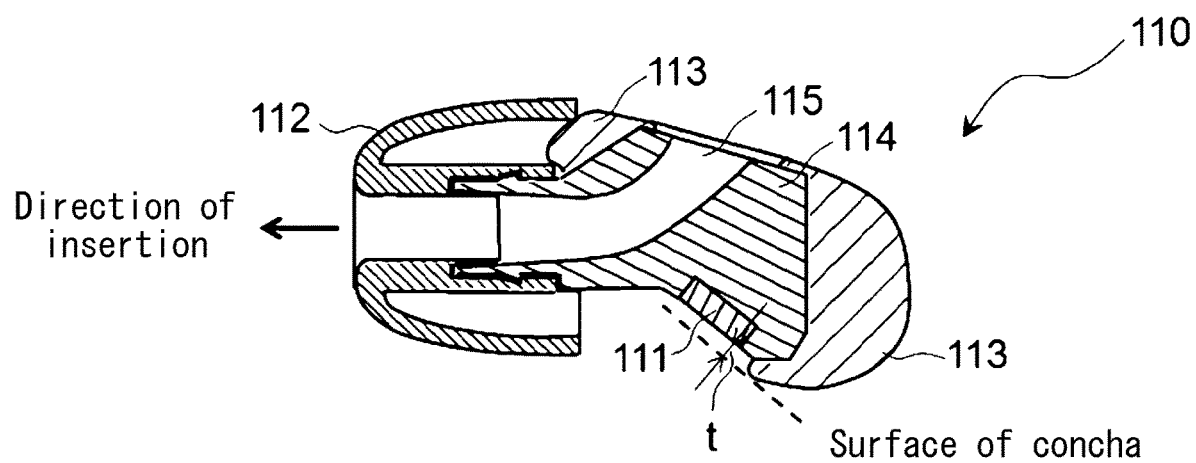
FIG. 2B schematically illustrates the cross-sectional shape of the biological information measurement apparatus according to Embodiment 1.

FIG. 2A schematically illustrates the structure of the earpiece 110 according to Embodiment 1. FIG. 2B is a schematic cross-sectional drawing when observing the A-A cross-section illustrated in FIG. 2A in the direction of the arrows. In FIG. 2A and FIG. 2B, the earpiece 110 is inserted in the user's external ear canal towards the left. The earpiece 110 is provided with the biological sensor 111, the insertion portion 112, a pad 113, and a housing 114. The biological sensor 111 is disposed inside the housing 114. Once the insertion portion 112 is inserted in the user's external ear canal, the biological sensor 111 is disposed so as to oppose the user's concha. The pad 113 includes an extension portion that is configured to be raised towards the concha from a surface of a first side of the housing where the biological sensor 111 is configured to face towards the concha, the pad 113 is positioned in contact with surfaces of second sides of the housing 114, and the second sides of the housing 114 include a side positioned opposite to the first side of the housing 114.

FIG. 2A schematically illustrates the structure of the earpiece 110 according to Embodiment 1. FIG. 2B is a schematic cross-sectional drawing when observing the A-A cross-section illustrated in FIG. 2A in the direction of the arrows. In FIG. 2A and FIG. 2B, the earpiece 110 is inserted in the user's external ear canal towards the left. The earpiece 110 is provided with the biological sensor 111, the insertion portion 112, a pad 113, and a housing 114. The biological sensor 111, insertion portion 112, and pad 113 are disposed inside the housing 114. Once the insertion portion 112 is inserted in the user's external ear canal, the biological sensor 111 is disposed so as to oppose the user's concha.

The biological sensor 111 is a pulse wave sensor and acquires pulse wave data from the user (living organism) as biological measurement output. The biological sensor 111 is provided with a optical emitter 111a and a optical detector 111b. In the biological sensor 111 according to this disclosure, for example a light emitting element such as a Light Emitting Diode (LED) is provided in the optical emitter 111a. In the biological sensor 111 according to this disclosure, for example a light detecting element such as a Phototransistor (PT) or a Photodiode (PD) is provided in the optical detector 111b. The biological sensor 111 measures pulse wave data by irradiating measurement light from the light emitting element onto the test site of the user's external ear canal and detecting reflected light from the test site with the light detecting element. In the case of measuring such light, the biological sensor 111 does not necessarily have to contact the site to be measured. The optical emitter 111a and optical detector 111b of the biological sensor 111 are arranged in parallel inside the housing, with a light-blocking wall therebetween. The light-blocking wall is disposed so that light emitted from the optical emitter 111a is not directly detected by the optical detector 111b. A protective, translucent panel is arranged in the biological sensor 111, and the inside of the biological sensor 111 is sealed off by the translucent panel.

The biological sensor 111 includes a driver (not illustrated). The driver drives the light emitting element and the light detecting element based on a measurement signal generated by the controller 120. The light emitting element and the light detecting element emit and detect light by being driven by the driver. Driving of the driver is, for example, controlled by the controller 120.

In the case of measuring pulse, the optical emitter 111a uses a blue (wavelength: 400 nm to 430 nm) or green (wavelength: 500 nm to 550 nm) LED or laser. Blue or green light of the aforementioned wavelength is easily absorbed by hemoglobin. The amount of absorbed light increases if the blood flow rate is high, and the output of the optical detector 111b weakens. A red (wavelength: 630 nm to 650 nm) LED or laser may also be used. In this case, since hemoglobin reflects red light, the amount of reflected light increases if the blood flow rate is high, and the output of the optical detector 111b grows stronger. PDs corresponding to the various wavelengths are used in the optical detector 111b.

The insertion portion 112 is disposed on the side of the housing 114 inserted into the external ear canal. When inserted into the external ear canal, the insertion portion 112 abuts the external ear canal. The user inserts the insertion portion 112 into the external ear canal so that the biological sensor 111 opposes the concha. When inserted into the external ear canal, the insertion portion 112 deforms in accordance with the shape of the external ear canal to attach firmly to the external ear canal. The earpiece 110 is held at a predetermined position of the ear by the insertion portion 112 attaching firmly to the external ear canal. The insertion portion 112 is formed from a material that has elasticity at room temperature and may, for example, be made of resin with a Shore hardness of approximately 30 to 60. The insertion portion 112 may, for example, be formed by silicone rubber, flexible polyurethane resin, or the like.

The pad 113 engages with the opposite end of the housing 114 from the side that is inserted into the external ear canal. In order to make it easier for the user to wear the earpiece 110, the pad 113 may be formed from a material having elasticity at room temperature, such as silicone rubber or flexible polyurethane resin. The pad 113 contacts the back side of the tragus and the back side portion of the antitragus, and together with the insertion portion 112, holds the earpiece 110 at a predetermined position of the ear. On the other hand, the space surrounded by the concha, the housing 114, and the biological sensor 111 is in a state (structure) in which light from the exterior cannot penetrate easily due to the outer peripheral portion of the pad 113. A portion of the pad 113 may be disposed at the periphery of the biological sensor 111. The pad 113 may be raised towards the concha from the surface of the biological sensor 111. For example, as illustrated in FIG. 2B, the pad 113 is raised towards the concha from the surface of the biological sensor 111 by a thickness of t mm. The thickness t mm may, for example, be approximately 0.5 mm to 3 mm. The pad 113 contacts the periphery of the concha around the biological sensor 111. The pad 113 prevents external light from being detected by the optical detector 111b when the biological sensor 111 acquires biological information. In order to further increase the light blocking effect, the pad 113 may, for example, be formed from light-blocking material such as black silicone rubber. The pad 113 may have a hollow structure so as to easily deform to match the size of the user's cavum conchae (the portion surrounded by the concha, the back side of the tragus, and the back side of the antitragus). The pad 113 prevents the earpiece 110 from deviating from a predetermined position even when the user exercises intensely. Furthermore, the pad 113 prevents light from entering into the optical detector 111b from the outside. Accordingly, a biological information acquisition apparatus according to this disclosure can acquire biological information with a higher degree of accuracy.

When the earpiece 110 is worn in the ear, the insertion portion 112 is engaged with the housing 114 at the side of the housing 114 inserted into the external ear canal. The biological sensor 111 is disposed in the housing 114 on a surface opposite the concha when the earpiece 110 is worn in the ear. When the earpiece 110 is worn in the ear, the pad 113 is engaged with the housing 114 at the opposite end from the side of the housing 114 inserted into the external ear canal. A vent 115 (air hole) is provided in the housing 114. The vent 115 is an air hole that opens to the outside of the ear from the external ear canal when the earpiece 110 is worn. The vent 115 may be formed as a hole in the housing 114 or be formed by recessing a portion of the housing 114. By the vent 115 being provided in the housing 114, the user can hear external sounds while measuring biological information, thereby improving user safety. The housing 114 may, for example, be formed from polycarbonate resin, amine-based resin, or the like. In this embodiment, the housing 114, insertion portion 112, and pad 113 engage to constitute the earpiece 110, but this disclosure is not limited to this configuration. The housing 114, insertion portion 112, and pad 113 may be formed integrally using the same material.

In the interior and exterior of the earpiece 110, various wires (not illustrated) are laid for power signals from the biological sensor 111 and to supply power to the biological sensor 111.

Referring again to FIG. 1, the controller 120 is a processor that controls overall operations of the biological information measurement apparatus 100. When the user measures biological information, the controller 120 measures the pulse as biological information based on pulse wave data acquired by the biological sensor 111.

For example, the controller 120 judges whether the pulse wave data, which is biological measurement output, are within an allowable range that can be used to measure biological information. When judging that the pulse wave data are not within the allowable range, the controller 120 provides notification of an error with the notification interface 150. Conversely, when judging that the pulse wave data are within the allowable range, the controller 120 provides notification with the notification interface 150 of the start of measurement.

The memory 160 may, for example, be configured with a semiconductor memory, a magnetic memory, or the like. The memory 160 stores a variety of information, programs for causing the biological information measurement apparatus 100 to operate, and the like. The memory 160 for example stores information (a threshold) on the allowable range that serves as the standard for judging whether the pulse wave data acquired by the biological sensor 111 can be used to measure biological information.

The communication interface 140 is connected to and communicates with a mobile phone via a wired connection or a wireless connection such as Bluetooth® (Bluetooth is a registered trademark in Japan, other countries, or both). The biological information measurement apparatus 100 for example transmits the biological information measured by the controller 120 to a mobile phone 200 via the communication interface 140.

The notification interface 150 notifies the user based on control by the controller 120, for example with a visual method using an image, characters, light emission, or the like; an auditory method using audio or the like; or a combination of these methods. In the case of providing notification with a visual method, the notification interface 150 may, for example, provide notification by displaying images or characters on a display device constituted by a liquid crystal display, organic EL display, inorganic EL display, or the like. The notification interface 150 may, for example, provide notification by causing an LED or other such light emitting element, separate from the biological sensor 111, to emit light. Notification by the notification interface 150 is not limited to a visual or auditory method. Any method recognizable by the user may be adopted.

The controller 120 may provide notification by, for example, displaying images or characters on a display 260 of the mobile phone 200 connected via the communication interface 140. In this case, the biological information measurement apparatus 100 need not be provided with the notification interface 150.

The controller 120, memory 160, notification interface 150, and communication interface 140 may be provided in the earpiece 110. Alternatively, the controller 120, memory 160, and notification interface 150 may be provided in the mobile phone 200, since it suffices for the biological information measurement apparatus 100 to be provided with at least the insertion portion 112 and the biological sensor 111.

The mobile phone 200 may, for example, be a smartphone and is connected to the biological information measurement apparatus 100. The mobile phone 200 includes a mobile phone controller 220, a communication interface 240, the display 260, and an input interface 270.

The mobile phone controller 220 is a processor that controls overall operations of the mobile phone 200. The mobile phone controller 220 may, for example, display the biological information measured by the biological information measurement apparatus 100 on the display 260.

The communication interface 240 is connected to and communicates with the biological information measurement apparatus 100 by a wired or wireless connection. The mobile phone 200 for example receives the biological information measured by the biological information measurement apparatus 100 via the communication interface 240.

The display 260 is a display device such as a liquid crystal display, an organic EL display, an inorganic EL display, or the like. The display 260 for example displays the biological information measured by the biological information measurement apparatus 100. The user can learn his own biological information by checking the display of the display 260.

The input interface 270 accepts operation input from the user and may be configured, for example, using operation buttons (operation keys). The input interface 270 may be configured by a touchscreen, an input region that accepts operation input from the user may be displayed on a portion of the display 260, and touch operation input by the user to this input region may be accepted.

Figure 3A:
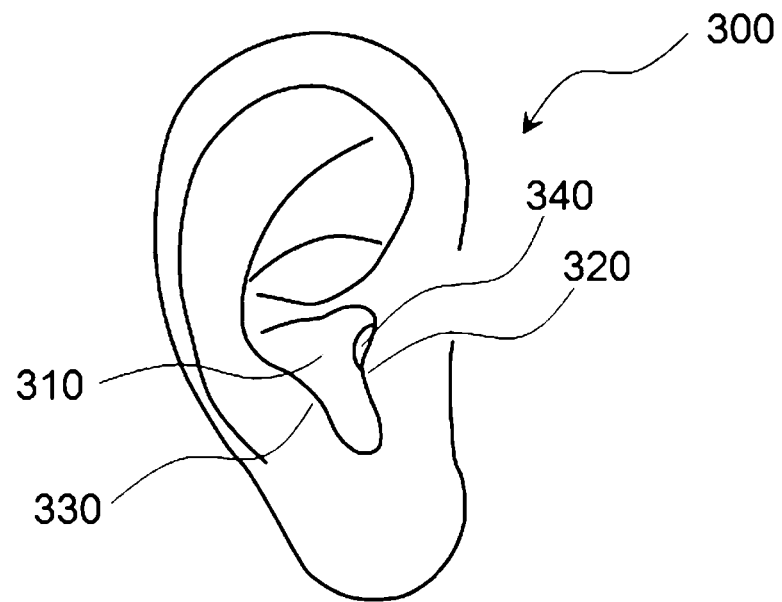
FIG. 3A schematically illustrates the structure of an ear.
Figure 3B:
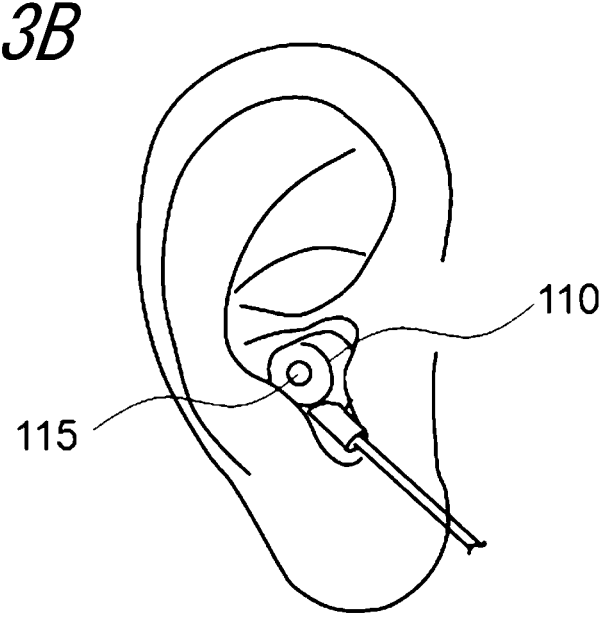
FIG. 3B illustrates the biological information measurement apparatus in FIGS. 2A and 2B as worn in an ear.

FIG. 3A schematically illustrates the structure of an ear. FIG. 3B illustrates the earpiece 110 of FIGS. 2A and 2B as worn in the ear. The biological information measurement apparatus 100 according to this disclosure measures biological information with the insertion portion 112 in the earpiece 110 being inserted in an external ear canal 340 so that the biological sensor 111 opposes a concha 310. The optical emitter 111a emits light towards the concha. The emitted light is reflected or scattered by the concha and detected by the optical detector 111b. The intensity of the reflected light varies in synchronization with the pulse. By observing this variation in the intensity of reflected light as a pulse wave, the pulse can be acquired. The portion of the concha that is measured is wider than, for example, the inner wall of the external ear canal. Accordingly, the degree of freedom for arranging the biological sensor 111 increases. For example, light can be emitted over a wider area by separating the optical emitter 111a from the concha rather than attaching the optical emitter 111a firmly to the concha. Also, the concha is flatter than, for example, the inner wall of the external ear canal. Accordingly, the direction of reflected light is constant, allowing the optical detector 111b to detect intense light stably. In this way, biological information over a wide area can be detected as intense light, thereby improving the measurement accuracy of biological information. Also, it is difficult for external light to penetrate into the space enclosed by the concha and the biological sensor 111, thereby improving the measurement accuracy of biological information.

Figure 4A:
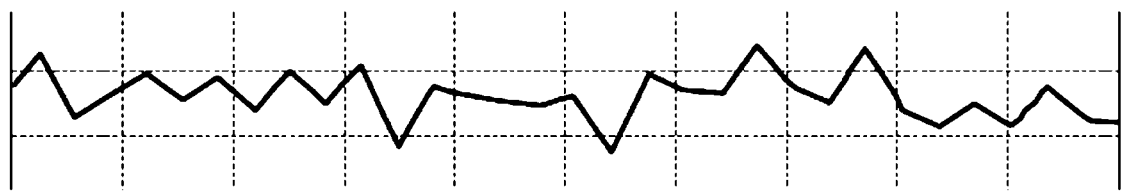
FIG. 4A illustrates an example of pulse wave data acquired by a known biological information measurement apparatus.
Figure 4B:
FIG. 4B illustrates an example of pulse wave data acquired by the biological sensor in FIG. 1.

FIG. 4A illustrates an example of pulse wave data acquired by a known biological information measurement apparatus. FIG. 4B illustrates an example of pulse wave data acquired by the biological sensor 111 according to Embodiment 1. In these figures of pulse wave data, the horizontal axis represents time, and the intensity of detected light is plotted along the vertical axis. In a known biological information measurement apparatus, a biological sensor provided with a optical emitter and a optical detector is abutted against the back side of the antitragus and acquires pulse wave data. The pulse wave data were measured after the subject performed a predetermined exercise for 5 minutes while wearing the biological information measurement apparatus. A comparison of FIG. 4A and FIG. 4B shows that in the pulse wave data in FIG. 4A, the period of the peaks is unstable, and the amplitude is small and inconsistent. By contrast, in the pulse wave data of FIG. 4B, the period of the peaks is stable, and the amplitude is large and consistent. The pulse wave data acquired by the biological sensor 111 according to Embodiment 1 clearly has better measurement accuracy than the pulse wave data acquired by a known biological information measurement apparatus. Confirmation of the state in which the known biological information measurement apparatus was worn after measurement revealed that the biological sensor which was abutted against the back side of the antitragus had become misaligned, allowing external light to enter the optical detector. By contrast, the biological information measurement apparatus 100 according to Embodiment 1 was worn in a stable state.

FIG. 5 compares the pulse measurement results for the biological information measurement apparatus 100 according to Embodiment 1 and a known biological information measurement apparatus. Pulse measurements were taken for 32 men and 18 women, for a total of 50 people. The known biological information measurement apparatus used a known method 1 to take measurements at a fingertip and a known method 2 to take measurements at the back side of the antitragus. The pulse was measured with the subject at rest. So that the subject state would not change, measurements were taken successively with the three methods for each subject.

The pulse acquisition rate is the probability that the pulse could be measured. The pulse acquisition rate was 100% for the biological information measurement apparatus 100 according to Embodiment 1. With the known method 1, the pulse acquisition rate was 96%, since an error occurred because of the pulse not being detectable due to poor circulation at the fingertip. With the known method 2, the pulse acquisition rate was 92%, since an error occurred because of the biological information measurement apparatus not being able to abut against the back side of the antitragus due to not matching the size of the ear.

The average pulse is the average of the pulse acquired for 50 people. The known method 2 yielded a higher average pulse than the other methods, suggesting a problem with measurement accuracy. A widely known cohort study yielded the results of an average pulse of 62±9.5 for 11,463 people. The average pulse measured by the biological information measurement apparatus 100 of this disclosure was 70.2. Since this value is within the range of the average pulse indicated by the cohort study, the value measured by the biological information measurement apparatus 100 according to Embodiment 1 can be deemed reliable.

Figure 6:
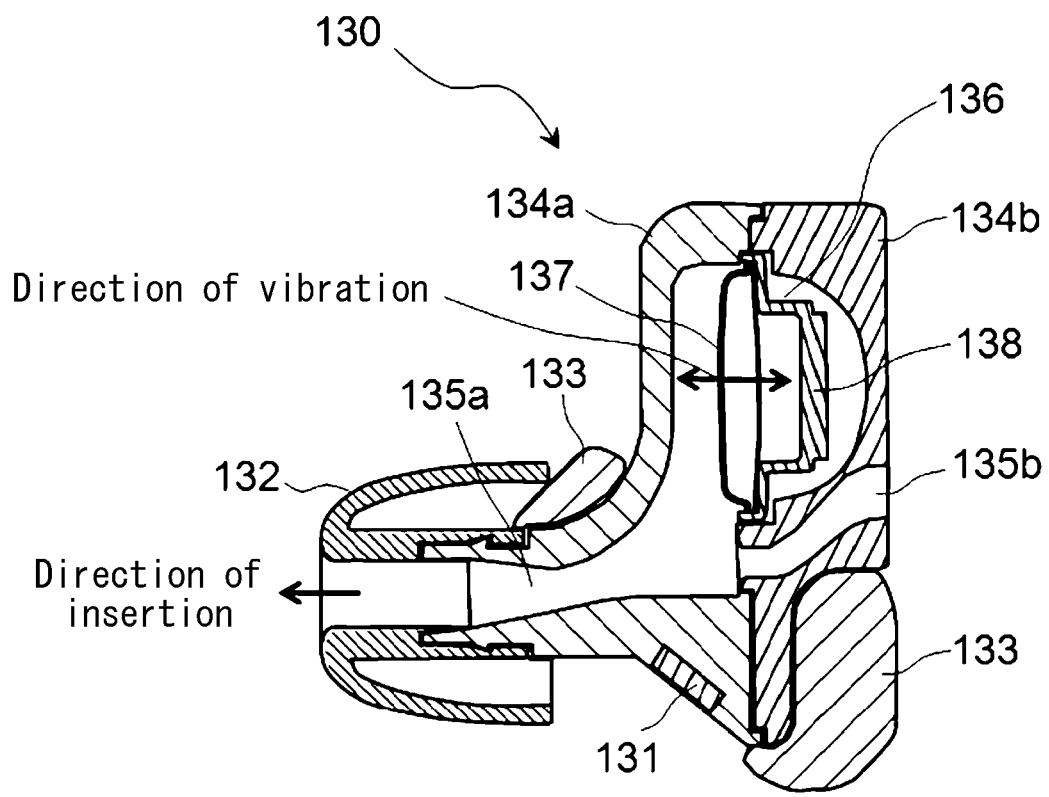
FIG. 6 schematically illustrates the cross-sectional shape of the biological information measurement apparatus according to Embodiment 2.

FIG. 6 schematically illustrates the cross-sectional shape of the biological information measurement apparatus according to Embodiment 2. The differences from the biological information measurement apparatus 100 according to Embodiment 1 are described below, with a detailed description of points that are the same being omitted.

The biological information measurement apparatus according to Embodiment 2 includes a speaker 136. The speaker 136 is formed by a diaphragm 137 and a driver 138. The speaker 136 is held in a housing 134b, and the housing 134b engages with a housing 134a. A vent 135a in the housing 134a and a vent 135b in the housing 134b are connected. With an earpiece 130 worn in the ear, the vent opens to the outside of the ear from the external ear canal. By the vent being provided, the user can hear external sounds while listening to music with the speaker, thereby improving user safety.

The sound produced by the speaker 136 is transmitted in the direction of insertion of an insertion portion 132 into the external ear canal, i.e. into the user's ear. The driver 138 vibrates the diaphragm 137 based on a sound signal of sound generated by the mobile phone 200. The diaphragm 137 vibrates based on driving by the driver 138 and reproduces sound. Driving of the driver 138 is, for example, controlled by the controller 120.

The direction of vibration of the diaphragm 137 is indicated in FIG. 6 by arrows. The speaker 136 is disposed so that the direction of insertion of the insertion portion 132 into the external ear canal and the direction of vibration of the diaphragm 137 are approximately parallel. The angle between the approximately parallel direction of vibration of the diaphragm 137 and direction of insertion of the insertion portion 132 is in a range of 0° to 10°. With this arrangement, reflection of sound decreases. Furthermore, vibration of sound is more easily transmitted to the eardrum. Also, upon wearing the earpiece 130 in the ear, the speaker is disposed outside of the ear. Therefore, a large speaker 136 can be selected without impairing the fit of the earpiece.

The speaker of this disclosure is not limited to being arranged in this way and may instead by disposed at the opposite end of the housing 134a, where the biological sensor 131 is disposed.

In the above embodiment, the biological information measurement apparatus has been described as measuring the pulse, but the measured biological information is not limited to this case. The measured biological information may, for example, be the rate of blood flow. When measuring the rate of blood flow, for example an infrared light (wavelength: 1.31 micrometers or 1.55 micrometers) laser may be used, and the relative rate of blood flow may be detected from the change in wavelength occurring due to the Doppler shift. The measured biological information may, for example, be body temperature instead. Body temperature is, for example, detected by thermal radiation (infrared radiation) outward from the concha. Body temperature may, for example, also be detected using a thermistor. When measuring rate of blood flow or body temperature as the biological information, the pad 113 functions as a light-blocking member while also functioning as a heat-blocking member. By including the pad 113, the biological information measurement apparatus is not easily affected by external temperature, allowing stable measurement of biological information.

The measured biological information may, for example, be blood pressure or the oxygen content of the blood. The biological information measurement apparatus is not limited to measuring one type of measured biological information and may measure a plurality of types of biological information by combining a plurality of sensors.

Although exemplary embodiments have been described with reference to the accompanying drawings, it is to be noted that various changes and modifications will be apparent to those skilled in the art based on this disclosure. Therefore, such changes and modifications are to be understood as included within the scope of this disclosure. For example, the functions and the like included in the various units and members may be reordered in any logically consistent way. Furthermore, units and members may be combined into one or divided.

The invention claimed is:

1. A biological information measurement apparatus comprising:
    a biological sensor configured to be disposed at a position opposite a concha, the biological sensor including an optical emitter;
    an insertion portion configured to be inserted in an external ear canal and configured to be in contact with an inner wall of the external ear canal;
    a housing configured to hold the biological sensor and the insertion portion; and
    a pad surrounding the housing, wherein
    the optical emitter is positioned on an outer surface of the housing, and is configured to face towards the concha, and the housing is positioned in an inside of the pad, and
    the pad includes an extension portion positioned between the housing and a surface of the concha, the extension portion forming a gap between the optical emitter and the surface of the concha when the insertion portion is inserted in the external ear canal and in contact with an inner wall of the external ear canal.

2. The biological information measurement apparatus of claim 1, further comprising a vent configured to be leading from the external ear canal to an exterior when the insertion portion is inserted in the external ear canal.

3. The biological information measurement apparatus of claim 1, wherein the optical emitter is further configured to emit light; wherein the biological sensor further comprises an optical detector configured to detect light; wherein the optical emitter is configured to emit light towards the concha, and the optical detector is configured to detect light returning from the concha.

4. The biological information measurement apparatus of claim 3, further comprising a light-blocking portion configured to prevent light other than the light returning from the concha from being detected by the optical detector when the insertion portion is inserted in the external ear canal and is in contact with the inner wall of the external ear canal.

5. The biological information measurement apparatus of claim 1, further comprising:
- a speaker configured to generate sound by vibrating a diaphragm;
- wherein a direction of vibration of the diaphragm is substantially parallel to a direction of insertion of the insertion portion.

\* \* \* \* \*